United States Patent [19]
Siess et al.

[11] Patent Number: 5,964,694
[45] Date of Patent: Oct. 12, 1999

[54] METHOD AND APPARATUS FOR CARDIAC BLOOD FLOW ASSISTANCE

[75] Inventors: Thorsten Siess, Aachen; Helmut Reul, Düren, both of Germany

[73] Assignee: Guidant Corporation, Menlo Park, Calif.

[21] Appl. No.: 08/881,884

[22] Filed: Jun. 24, 1997

Related U.S. Application Data

[62] Division of application No. 08/832,040, Apr. 2, 1997.
[51] Int. Cl.[6] .................................................. A61M 1/12
[52] U.S. Cl. .................................. 600/17; 623/3; 415/900
[58] Field of Search .......................... 600/16, 17; 623/3; 415/900; 417/423.3, 423.14, 44.2

[56] References Cited

U.S. PATENT DOCUMENTS

| 4,688,998 | 8/1987 | Olsen et al. | 600/16 |
| 5,385,581 | 1/1995 | Bramm et al. | 600/16 |

*Primary Examiner*—William E. Kamm
*Assistant Examiner*—George R. Evanisko
*Attorney, Agent, or Firm*—Fulwider Patton Lee & Utecht, LLP

[57] ABSTRACT

An intravascular microaxial pump has an integrated configuration that enables both the drive unit as well as the pumping segment to be advanced through a patient's vasculature. The device includes elements that enhance pumping efficiency and performance while minimizing shear and cavitation. Cost reduction is achieved in the reusability of certain components while a manufacturing method reduces the labor involved in the pump's assembly.

7 Claims, 10 Drawing Sheets

METHOD AND APPARATUS FOR CARDIAC BLOOD FLOW ASSISTANCE

This is a divisional of copending application Ser. No. 08/832,040 filed on Apr. 2, 1997.

BACKGROUND OF THE INVENTION

The invention generally relates to intravascular flow pumps and more particularly pertains to a pump configuration wherein a pumping segment and drive unit are combined along a common axis.

Intravascular flow pumps have previously been described which are introduced into the body by puncturing a vessel in the vascular system and then advanced through such vessel to the site where fluid is to be pumped. The maximum diameter of any components that are introduced into the vessel is limited so as to facilitate their passage through the entire vessel path between the point of entry and the pumping site. Additionally, maximum rigid length must be limited so as to permit the device to be maneuvered around the bends and convolutions that may be encountered along such vessel path. In the case of a blood pump used for left ventricular support for example, such limits have been found to be about 8.0 mm in diameter and 6 cm of rigid length to ensure uninhibited passage up the femoral artery, around the aortic arch and into the heart. In the case of a blood pump used for right ventricular support, such limits have been found to be about 15 mm in diameter and 10 cm of rigid length to insure uninhibited passage up the femoral vein and up through the interior vena cava into the right atrium of the heart. Intravascular pumps may also be placed surgically into the left ventricle either via an aortotomy in retrograde placement across the valve or into the right ventricle via artereotomy in the pulmonary artery and placed retrograde through the pulmonary valve or from the vena cava through the right atrium, right ventricle and pulmonary artery. Such techniques similarly require the rigid length to be minimized so as to facilitate placement. Additionally, it is most desirable to be able to monitor the positioning of the pump relative to the anatomy in order to optimize performance and to prevent injury.

As is described in EP 0 157 871 B1 and EP 0 397 668, intravascular heart pumps are known, in which the pumping segment is driven by a remotely disposed drive unit. The impeller, which is rotatably disposed in a tubular housing, is linked with an extracorporeal drive unit by a flexible shaft or cable which runs through a catheter. The drive unit rotates the flexible shaft which, in turn, drives the pumping segment. Such configuration enjoys certain advantages due to the extracorporeal location of the drive unit in that the drive unit is not subject to a size limitation and therefore does not need to have a high specific power output. Additionally, any heat generated by the drive unit does not impact the patient and because the unit does not contact the patient, it can readily be reused. In an effort to reduce friction between the shaft and the catheter, continuous lubrication is necessary, with the attendant risk that a portion of such lubricant, may pass through the seals of the pump unit and into the blood stream. In addition, the flexible shaft precludes access to those places in the body where excessively sharp bends of the drive shaft would be necessary.

The blood pump described in WO 94/09835 provides for temporary support of the heart. Such blood pump, which is used on the surgically opened heart, has a cylindrical housing which contains the motor and the pump, however, only the pumping segment is positionable within the aorta while the motor portion remains outside the vessel. An intravascular blood pump is described in EP 0 157 859 B1, in which the motor portion and the pump portion are structurally united. Although such device is implantable, it is not however advanceable through the vasculature to the pumping site and its implantation therefore requires a fairly invasive procedure.

More recently, miniaturized drive units and pumping segments have been combined to provide intravascular pumps. However, a number of challenges are inherent in the necessary miniaturization of the components. For example, it is necessary for the drive unit to have an extremely high specific power output yet its surface temperature must never exceed 40° C. in order to avoid denaturization of albumin and/or tissue damage. Moreover, due to the limited amount of power that is available from a miniaturized drive unit and due to the size reduction in the pumping segment that is necessary in order to accommodate the drive unit in the limited amount of space that is available, the pumping segment must be especially efficient, capable of pumping fluids at substantial flow rates for extended periods of time. In the event a relatively fragile fluid such as blood is to be pumped, it is imperative that the required flow rate is achieved without shear and/or cavitation so as to prevent excessive hemolysis. Additionally, flow over the surfaces of the pump must be managed so as to avoid distorted flow pattern or areas of low flow in order to prevent thrombogenisis. Furthermore, in order to maintain optimum performance, it is necessary to stabilize the position of the device to prevent radial, axial and/or rotational movement. It is additionally most desirable to be able to continually monitor the pump's position and performance in order to determine whether any adjustments are necessary.

The presence of the drive unit within the body requires its interior to be properly sealed so as to prevent the transfer of fluids from within the drive unit into the patient or the incursion of fluids from the patient into the drive unit. The former contingency could have a toxic or embolic effect on the patient while the incursion of fluid into the drive unit would result in reduced performance and could damage the internal components. Adequate sealing of the drive unit must however be balanced against any increases in energy demand or by any compromise of its durability and thrombogenicity. Finally, it is most desirable to minimize the costs associated with the use of intravascular flow pumps either by reducing manufacturing costs and/or by maximizing the number of reusable components.

Thus, there is a need for an improved intravascular microaxial pump that is capable of reliably, safely, and efficiently pumping fluids for extended periods of time at high flow rates without cavitation, intolerable shear or heat build-up.

SUMMARY OF THE INVENTION

The pump of the present invention overcomes the shortcomings of previously known microaxial intravascular pump devices. The integrated configuration provides a number of benefits including the elimination of a flexible drive shaft along with the problems and limitations inherently associated therewith. Additionally, the substantially constant diameter of the entire device facilitates the placement of the drive unit/pumping segment combination completely within the vasculature. Furthermore, in the percutaneous placement of the device, it can more easily be advanced past sharp bends in a patient's vasculature that would preclude power transfer thereacross via a flexible drive shaft. The inherent versatility of such configuration allows it to be adapted for use in either the right or the left ventricles or in both ventricles simultaneously.

The device of the present invention employs an electric micro motor contained in the drive unit that rotates an impeller disposed in the attached pumping segment. The drive unit is positioned proximally to the pumping segment and is coaxially aligned therewith. The temperature of the motor surface is important to control. Motor surface temperature is a function of motor power dissipation, coolant flow over the motor and motor surface area. This temperature is optionally monitored by a sensor attached to the motor surface. By directing the flow of pumped fluid over the surface of the drive unit, heat is continually removed therefrom enabling an acceptable temperature level to be maintained at all times. A catheter extending proximally from the drive unit has electrical conduits extending therethrough to allow the operation of the drive unit to be monitored and controlled. In the case of percutaneous applications, the catheter enables the device to be maneuvered within the vasculature.

Leakage of fluid into and out of the drive unit is controlled in a number of different ways. In one embodiment the interior of the drive unit is sealed by an annular cup-shaped seal fitted about the rotating drive shaft that extends outwardly from within the drive unit. Alternatively, two such seals are employed in tandem in order to provide an effective backup in the event one or the other seal fails. The drive unit is internally configured to minimize the void space therein and as a result, the volume of any fluids contained in the drive unit is reduced. Thus, the amount of fluid that could enter the patient in the event of seal failure is commensurately reduced. In one embodiment, the interior of the device is sealed at a pressure that is somewhat lower than the pressure that the surrounding pumped fluid is expected to exert on the drive unit. As a result, any leakage that may occur would result in the less onerous alternative of fluid incursion into the drive unit rather than fluid leakage into the patient. Alternatively, the interior is charged with a biocompatible fluid whereby any leakage from the drive unit into the patient is rendered tolerable. By additionally pressurizing the biocompatible fluid contained within the drive unit to a level that exceeds the exterior pressure that is expected to be encountered during its operation, fluid incursion into the drive unit is effectively prevented. Fitment of a flexible diaphragm to the drive unit's exterior surface so as to be in fluid communication with its interior provides a visual indication as to the state of charge.

Alternatively, biocompatible purge fluid is continually supplied to the drive unit and is caused to flow across the seal. This provides the two fold advantage of positively preventing fluid incursion into the pump and continually lubricating the seal surfaces to extend service life and minimize risk of thrombi formation related to dissipation in the seal.

In an alternative embodiment, the drive unit is hermetically sealed which is made possible by the elimination of a direct coupling between the electric motor and the impeller. Instead of a rotating drive shaft, the impeller is magnetically coupled to a magnetic rotor that is rotated within the drive unit. The magnetic coupling not only serves to impart rotation to the impeller but also serves to retain the impeller on a fixed shaft. The impeller is supported near its distal end by a bearing that facilitates rotation and allows the impeller to automatically center itself thereby enabling the device to attain extremely high rotational speeds. A small portion of the pumped fluid is directed between the impeller hub and the fixed shaft to dampen any axial movement thereof.

In order to enhance the pumping efficiency of the microaxial pump configuration employing a rotating shaft that protrudes from the drive unit to rotate the impeller within the pump housing, the drive shaft is supported by bearings positioned at the extreme ends of the drive unit. As a result, the precise and stable alignment of the shaft is possible to preclude impeller-to-pump housing contact even at very high rates of rotation. Minimizing acircular excursions of the impeller additionally serves to prevent hemolysis during the pumping of blood. Combining the seal and bearing allows the shaft to be supported at a position immediately adjacent to the impeller hub.

In an alternative embodiment, the fixed pump stator is eliminated in order to broaden the operating range of the pump device. This is especially advantageous in order to accommodate the pulsatile nature of the combined output of the pump and the heart in blood pumping applications. Additionally, deletion of the stator reduces hemolysis and eliminates a major site for clot formation. The lack of stator also has the effect of shortening the rigid length of the device and thereby enhances its maneuverability.

In order to further enhance the efficiency of the pumping segment, features are optionally incorporated therein that stabilize its axial, radial and rotational position during operation. Pumping losses are reduced by elements that seal the device relative the surrounding vessel walls so as to prevent backflow.

In order to more effectively and efficiently operate the pump, sensors are incorporated in the device to provide data as to its function. Sensors are provided by which its actual position can be monitored in order to permit prompt adjustment if it is deemed necessary. The sensors additionally allow the performance of the pump and the patient to be monitored in real time. With the availability of data indicative of, but not limited to, inlet pressure, discharge pressure and the load imposed on the electric motor, the performance of the pump can be fully monitored and optimized with respect to the patient. Multi-pump systems benefit greatly from such data gathering capability to enable the coordinated flow of fluid through a body system to be optimized.

Finally, the device incorporates features that minimize the costs involved. In one embodiment, the device is configured to allow the most expensive components to be sterilized and reused while only the relatively inexpensive components are disposed of. Additionally, multiple components of the drive unit are assembled and then integrated within a molding to reduce the number of parts and obviate the labor intensive assembly and alignment of a multitude of small machined parts.

These and other features and advantages of the present invention will become apparent from the following detailed description of a preferred embodiment which, taken in conjunction with the accompanying drawings, illustrates by way of example the principles of the invention.

DETAILED DESCRIPTION OF THE PREFERRED EMBODIMENTS

The figures generally illustrate various preferred embodiments of the intravascular microaxial pump of the present invention. The pump or pumps are introduced into a patient's vasculature either by surgical implantation therein or by advancement therethrough to a location where fluid is to be pumped. The device is not limited to the pumping of any particular type of fluid nor for use at any one particular location in the body.

Figure 1:
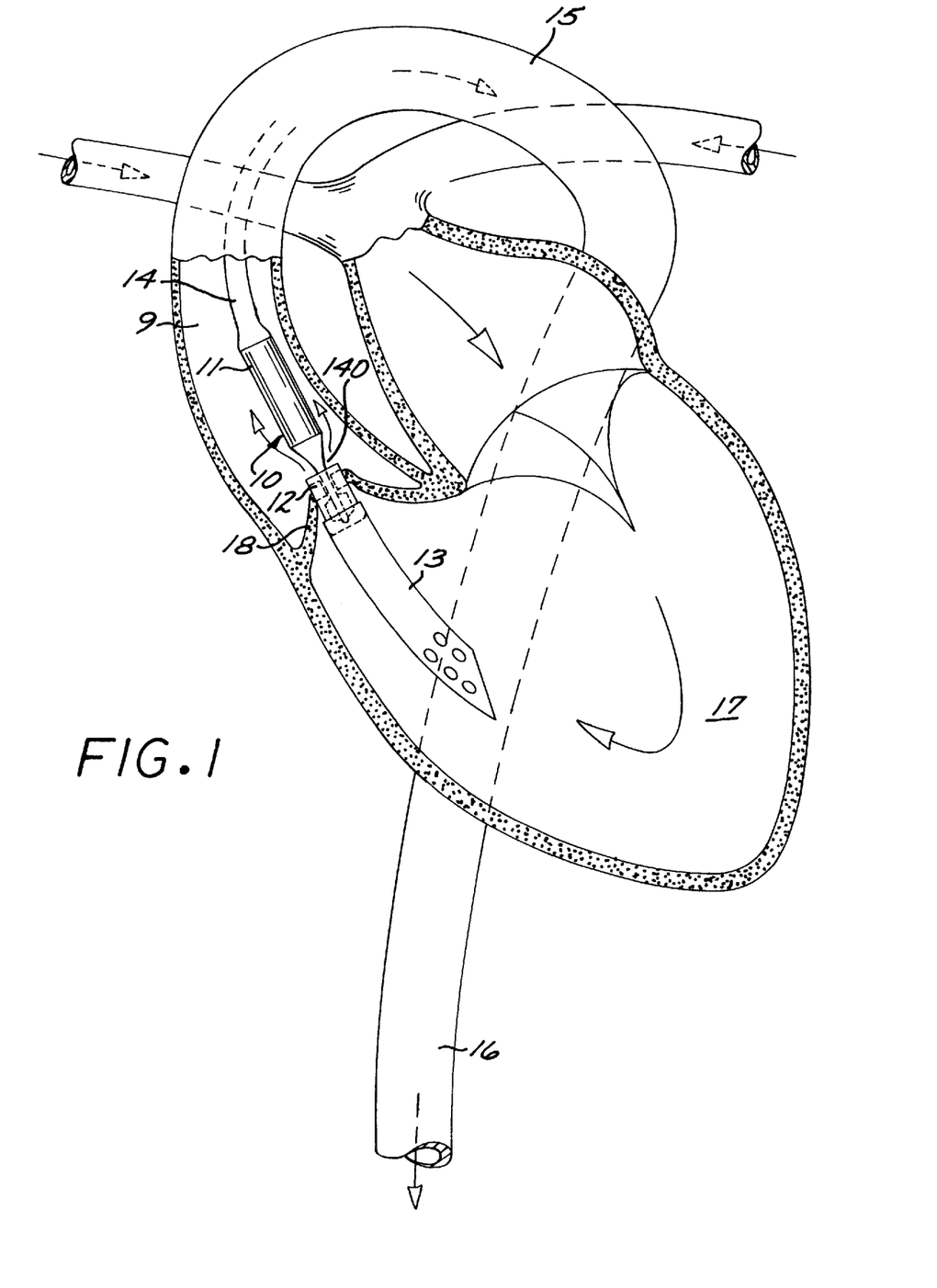
FIG. 1 is a schematic illustration of a device according to the present invention positioned in the heart.

FIG. 1 depicts an exemplary application of the microaxial pump of the present invention wherein the pump is being utilized to pump blood and more particularly, to provide left ventricular support wherein blood is pumped from within the ventricle out into the aorta. The microaxial pump 10 includes a drive unit 11 and a pumping segment 12, which are arranged coaxially one behind the other to yield a generally cylindrical structure. Distally extending from the pumping segment is an inlet cannula 13, which has openings formed in its distal end as well as its sides to permit entry of fluid into the pump. The proximal end of the microaxial pump 10 is connected to a catheter 14, which has been inserted via the femoral artery through the aortic arch 15 and into the ventricle 17. The microaxial pump 10 is positioned primarily in the ascending aorta 9, such that the straight, short inlet cannula 13 protrudes into the heart chamber 17. The aortic valve 18 is in the closed state either sealed about the outside of the pumping segment or about the inlet cannula. The microaxial pump 10 with the front-mounted inlet cannula 13 is advanced into the position depicted by manipulation of the catheter 14, that extends proximally therefrom possibly with the aid of a guide wire. Once in position, blood is drawn from the ventricle through the inlet cannula 13, through the pumping segment, and pumped out over the drive unit into the aorta 16.

Figure 2:
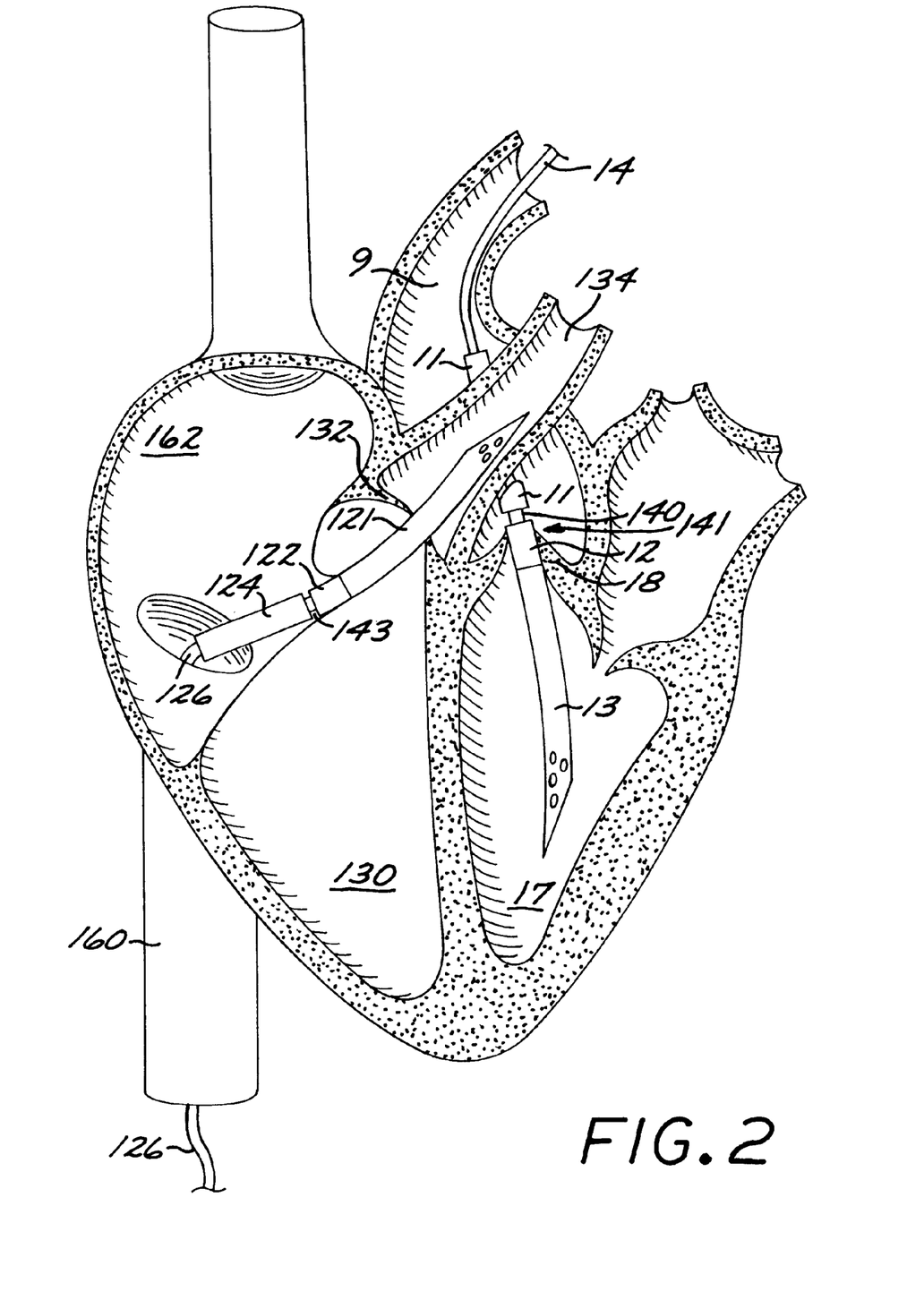
FIG. 2 is a schematic illustration of a preferred method of positioning multiple devices of the present invention in the heart.

FIG. 2 illustrates a preferred method of using the pump configuration generally described in FIG. 1, and requires the simultaneous placement of two pumps in the heart with the capability of assuming total circulatory support. Both pumps are shown as having been percutaneously placed wherein the catheter 14 of the left pump 141 extends through the vasculature exiting through a peripheral artery while the right side pump catheter 126 extends through the venous vasculature exiting through a peripheral vein. In this particular application, the left pump 141 is positioned and is operated precisely as described above and shown in FIG. 1. The right side pump 122 is operated in a reverse flow manner wherein fluid is drawn in over the drive unit 124 into port 143 and out through cannula 121. As a result, blood is drawn from either the right atrium 162 or the right ventricle 130 and is discharged into the pulmonary artery 134. The right outlet cannula 121 is positioned across the pulmonary valve 132 and into the pulmonary artery 134.

Figure 3:
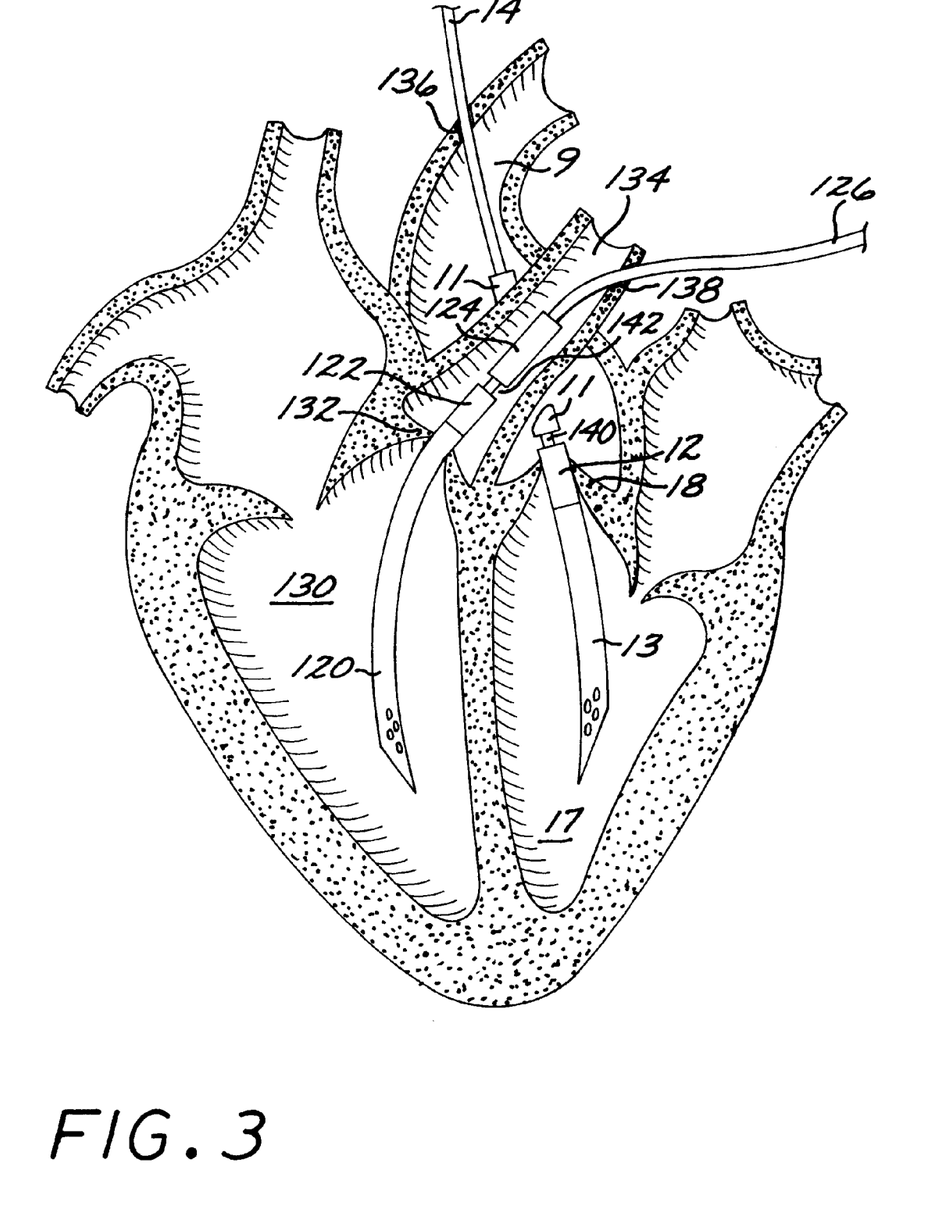
FIG. 3 is a schematic illustration of an alternative method of positioning multiple devices of the present invention in the heart.

FIG. 3 illustrates an alternative method of placing two pumps in the heart with the capability of assuming total circulatory support. Both pumps are shown as having been surgically implanted wherein the catheter 14 of the left pump 141 extends through the aortic wall at 136 while the right side pump catheter 126 extends through the pulmonary artery 134 at 138. The left inlet cannula 13 is positioned within left ventricle 17 and sealed by the aortic valve 18 distal to the discharge port 140. The right inlet cannula 120 is positioned within right ventricle 130 and sealed by the pulmonary valve 132. Both pumps are operated so as to draw blood in through cannulas 13, 120 and discharge via port 140, 142.

Figure 4:
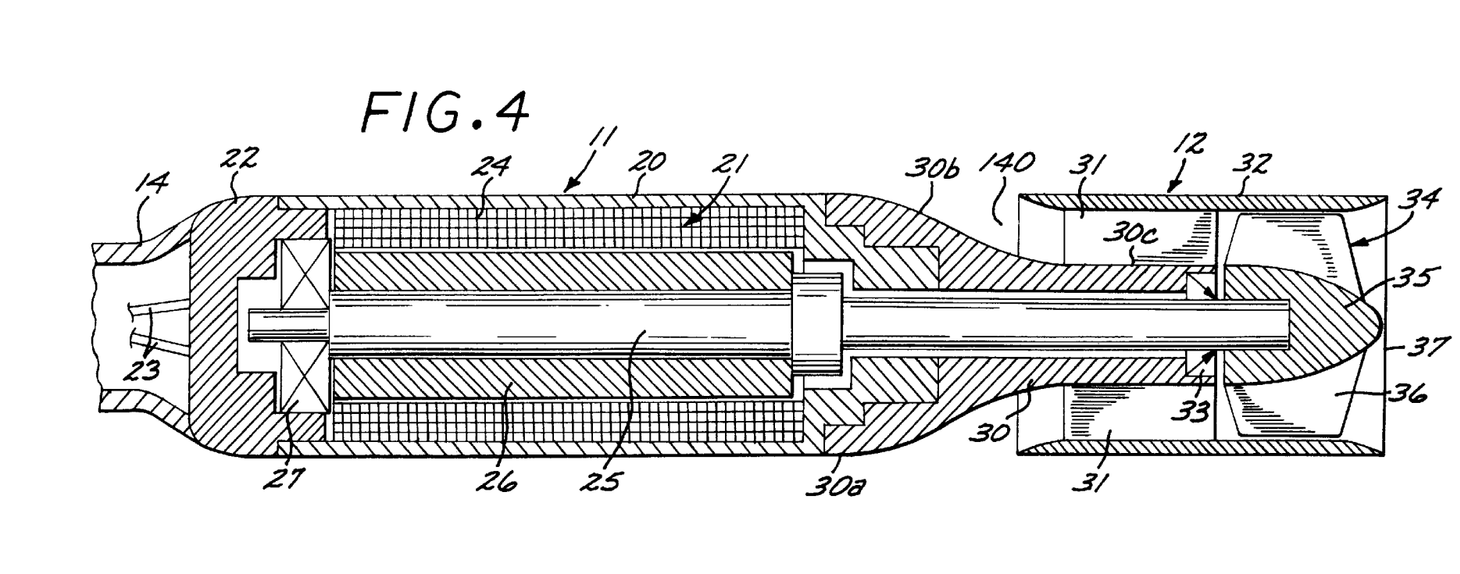
FIG. 4 in a longitudinal cross-section of an embodiment of the present invention.

FIG. 4 depicts a preferred exemplary embodiment of the microaxial pump clearly showing the drive unit 11 and the pumping segment 12 rigidly attached to one another. The drive unit 11 has an elongated cylindrical housing 20 in which the electric motor 21 is disposed. On the proximal end, the housing 20 is sealed by an end wall 22 to which the flexible catheter 14 is sealingly connected. The electrical conduits 23 that supply power and with which the electric motor 21 is controlled extend through the catheter 14.

The electric motor is an electronically commutated synchronous device wherein the stator 24 consists of small ferritic ring-shaped layers and of interior windings as is well known in the art. The stator 24 is solidly attached to the interior of motor housing 20, surrounds the rotor 26 and is dimensioned to leave an air gap of about 0.1 mm therebetween. The rotor, consisting of permanent magnets magnetized in the circumferential direction, surrounds and is rigidly attached to the shaft 25. Such shaft is supported at its proximal end by bearing 27 which is embedded in either the motor housing or in the end wall 22. The shaft extends through the entire length of the motor housing 20 and protrudes from its distal end to serve as the drive shaft.

The distal end of the motor housing 20 forms a tube 30 which has the same diameter on its proximal end 30a as the cylindrical housing 20 and is sealingly connected thereto. A tapering section 30b extends distally therefrom wherein its external diameter gradually reduces down to that of the cylindrical distal end section 30c. The taper is contoured to promote the smooth flow of pumped fluid thereover. Radial ribs 31, whose outer ends support the cylindrical tubular pump housing 32, extend radially outwardly from the end section 30c of the tube 30 and serve as fixed stator elements to direct the flow of fluid discharged from the adjacent impeller 34. Shaft 25 is supported at the extreme distal end of section 30c by bearing 33 which also serves as a seal. Precise alignment and stable concentric operation of the shaft are obtained by the location of the bearings 27 and 33 at the extreme ends of the shaft 25. It is particularly advantageous that the front bearing 33 is located as close to the impeller 34 as possible. The high rotational speed of the drive unit requires the use of very low friction bearings and seals. In certain applications, it may be desirable to separate the sealing function from the bearing in function, thereby requiring a configuration other than that shown in the Figures.

The shaft 25 extends distally from tube 30 and supports hub 35 on its distal end. Vanes 36 or pump blades extend outwardly from the hub to form the impeller 34. The impeller 34 is configured such that upon rotation, fluid is drawn in through the front intake opening 37 of the pump housing 32 and driven proximally within the pump housing 32. The fluid flows past the stator blades 31 and outwardly through the annular gap between the pump housing 32 and the motor housing 20 along the section 30b of the tube 30 and over the outer surface of the motor housing 20 thereby serving to remove any heat generated by the drive unit. The motor housing 20 and the pump housing 32 have roughly the same diameter in the embodiment illustrated, however, the external diameter of the pump housing 32 may be somewhat larger than that of the motor housing, since the pumped fluid must pass through rather than over the housing and any backflow between its external surface and the vessel walls is counterproductive.

In order to minimize the void space and hence the volume of fluid in the drive unit, the motor housing and all internal components are configured so as to provide only the minimum mechanical clearances necessary for assembly and for uninhibited rotation. Due to the drag imposed by liquids, it is desirable to fill the void space within the drive unit with a gas. Alternatively, if the charge fluid is selected to be a liquid, clearance dimensions are somewhat relaxed to accommodate the liquid. Allowances are made for typical manufacturing tolerances, differential thermal expansion and the effect of expected mechanical stresses. The amount of fluid that could escape into the patient in the event of seal failure is thereby minimized. The risk is further reduced by sealing the drive unit at ambient atmospheric pressure. Subsequent use within the body assures a negative pressure differential even when fluids contained within the drive unit are heated by the operation of the device. As a result, seal failure would merely cause incursion of bodily fluid into the drive unit rather than the leakage of fluid from the drive unit into the patient. The use of a preloaded low friction U-cup dynamic seal on the motor shaft exhibits good sealing characteristics at low differential pressures. As is shown in FIG. 5, the seal is oriented such that the high pressure side is on the fluid side while the low pressure side is oriented toward the interior of the motor.

Figure 5:
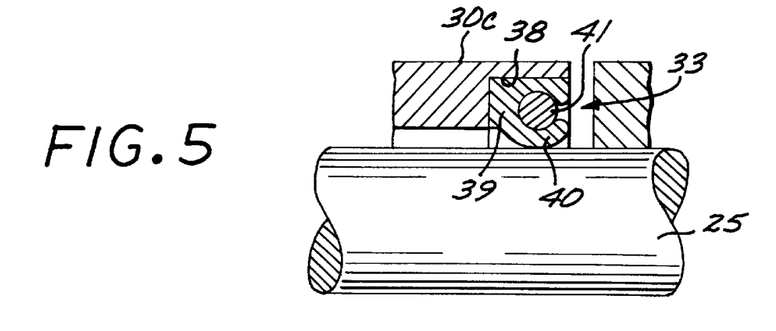
FIG. 5 is an enlarged view of circled section III of FIG. 4.

FIG. 5 is an enlarged view showing the seal/bearing element seated within recess 38 which is open toward the shaft and toward the distal end. The bearing body 39 is made of polytetrafluoroethylene [TEFLON], which has a high hardness and a low coefficient of friction with the surface of drive shaft 25. The sealing bead 40, disposed on its inner surface surrounds the rotating shaft 25 along a single line. A spring element 41, positioned in the interior of the bearing body 39, presses the bead area 40 against the shaft 25 so as to maintain a seal. Combining the sealing and support function in a single component allows the bearing to be positioned as close to the impeller as possible.

Figure 6:
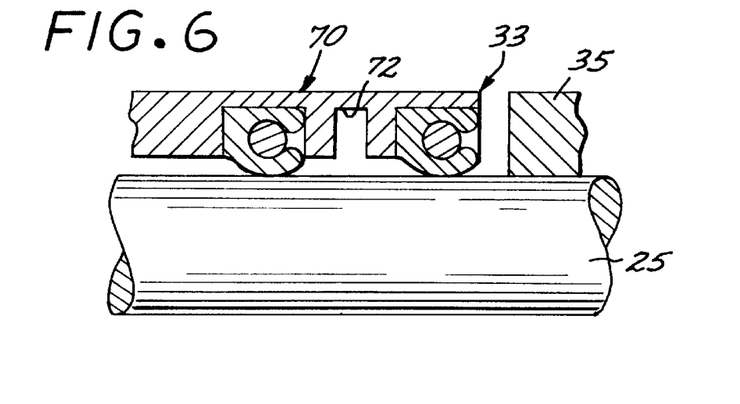
FIG. 6 is an enlarged view of an alternative embodiment of the seal configuration shown in FIG. 5.

Alternatively, the double seal configuration shown in FIG. 6 may be employed wherein the secondary seal 70 improves overall sealing reliability. Additionally, the small void volume 72 disposed between the primary 33 and secondary seal 70 is filled with a small amount of biocompatible lubricant that is retained therein to keep initial seal friction very low and improve seal life. In the event the primary seal fails, bodily fluids entering the device would be retained within the void space and prevent the motor from being damaged. On the other hand, if the primary seal were to fail catastrophically, only a small amount of the biocompatible lubricant would enter the patient while the fluids present within the motor would be contained by the secondary seal. In the embodiment shown, the secondary seal is identical to the primary seal. In the event friction levels must be reduced, a secondary seal with a lower sealing force and thus lower friction may be employed.

As a further alternative, especially advantageous for long-term applications, wherein extended service life of the drive unit is critical, the void space within said drive unit is filled during the assembly process with a gas at slightly superatmospheric pressure. The gas is selected for its chemical inertness to protect the internal motor components as well as for its biocompatibility and its ability to be quickly absorbed in the pumped fluid in the event the seal leaks or fails. In the event of seal failure, the superatmospheric pressure would result in transfer of benign gas to the pumped fluid and thereby protect the motor from fluid incursion and damage.

Figure 7:
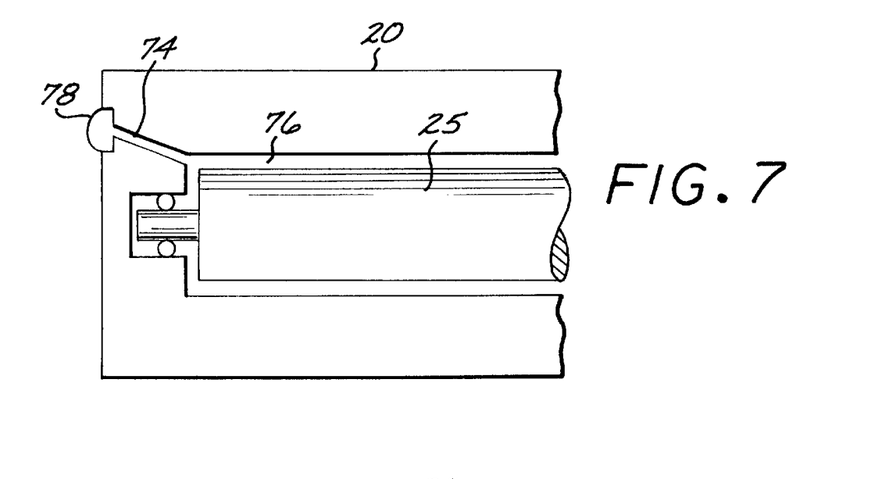
FIG. 7 is a schematic illustration of a drive unit incorporating a visual charge indicator.

A further feature advantageous for use in drive unit configurations incorporating the superatmospheric gas charge described above is illustrated in FIG. 7. The motor housing 20 incorporates an internal conduit 74 for setting the void space 76 within the drive unit into fluid communication with a flexible diaphragm 78 disposed on the surface of the housing. Upon pressurization, the diaphragm becomes domed to provide a visual indication as to the state of charge. The diaphragm additionally serves as a reservoir of gas or other charge fluid and thereby extends the shelf life of the device.

Figure 8:
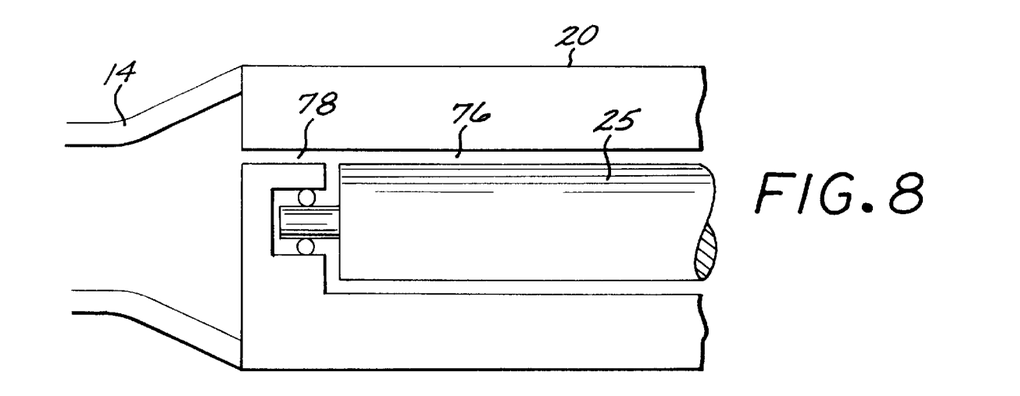
FIG. 8 is a schematic illustration of a drive unit incorporating a purge system.

Alternatively, the interior of the drive unit is set into fluid communication with the catheter 14 via duct 78 as is schematically shown in FIG. 8, whereby the void space 76 within the drive unit is continually supplied with a biocompatible purge fluid such as water sterilized from an extracorporeal source (not shown). The purge fluid is pressurized so as to maintain a slow purge rate over the seals of about 1–5 ml/hr. This precludes the incursion of bodily fluid into the drive unit and additionally extends the service life of the seals as the purge fluid continually lubricates the rotating seal interface as it is slowly forced thereacross. Because of the high rotational speed of the motor, clearance dimensions are somewhat relaxed to accommodate the presence of the purge fluid and thus reduce drag. In the event a purge fluid is selected that is not chemically inert with respect to the components within the drive unit, such components are coated with a thin environmental seal such as paralyene.

Figure 9:
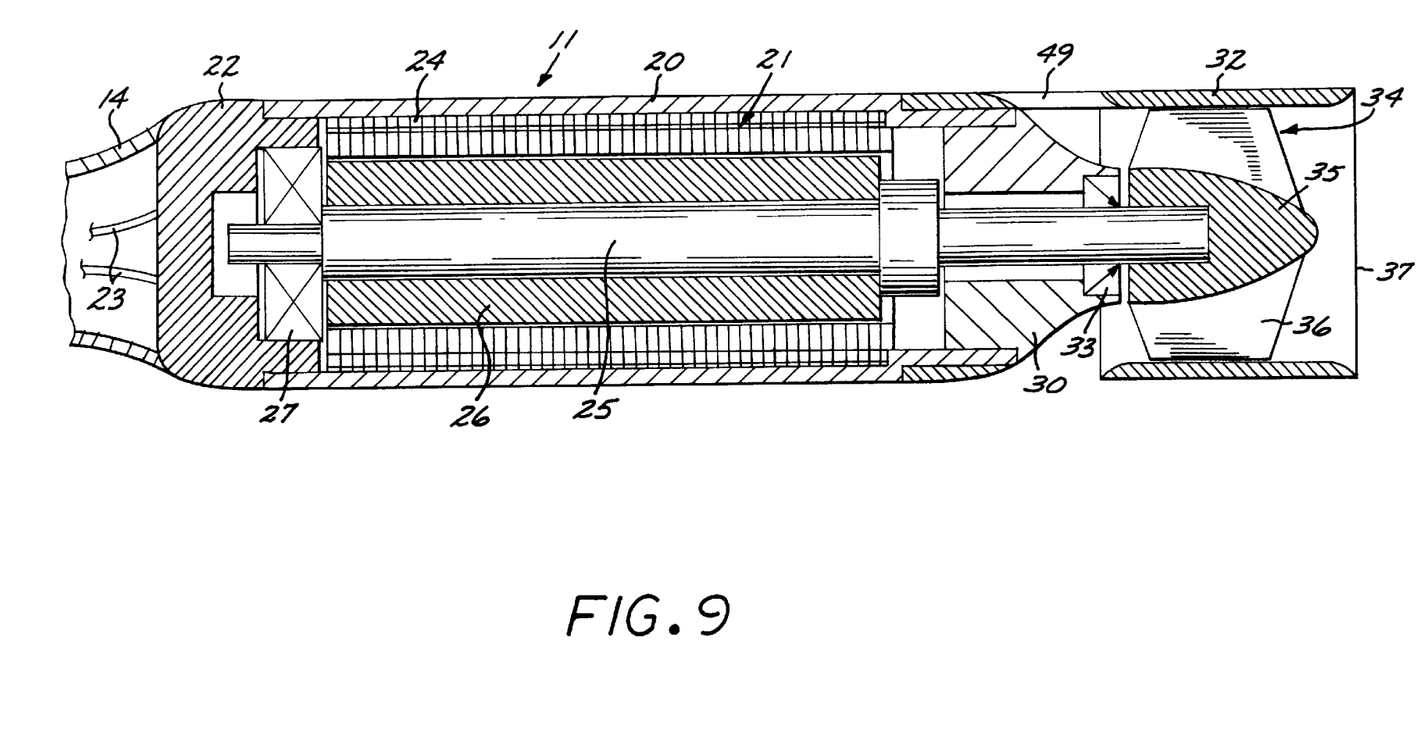
FIG. 9 is a longitudinal cross-section of a statorless embodiment of the present invention.

FIG. 9 illustrates an alternative embodiment wherein the pumping segment is devoid of a pump stator. While the presence of a stator is useful in optimizing pumping efficiency at a specified design point (flow rate and pressure) and enhancing the maximum pressure head, it has been found that operation of such pump can rarely be held at such design point. This is especially true when the pump is utilized in a supporting role for the heart where a wide range of flow and pressure conditions may be encountered and the pulsatile nature of the heart output continually varies these parameters. Operation of the pump well outside the design point yields a mismatch of flow velocity entrance angles with respect to the entrance angle to a particular stator. This results in flow separation which, in the event the pumped medium is blood, causes higher hemolysis and more significantly, can cause thrombus formation in these regions. By eliminating the stator, a much broader efficiency range is achieved albeit with a reduced peak efficiency value. Although the radial flow component increases without a fixed stator, it has been found that no significant increase in turbulence results that would cause dislodgement of clots and plaque from the arterial wall. In comparing the statorless embodiment illustrated in FIG. 9 to the embodiment that includes a stator 31 illustrated in FIG. 4, it is apparent that the length of the cylindrical distal end section 30c has been significantly reduced. This has the effect of commensurately reducing the rigid length of the entire pump device. The pump housing 32 is connected to the motor housing 20 by at least three slender longitudinally oriented supports 49. An additional advantage inherent in a statorless configuration is its ready adaptability to reverse flow conditions.

Figure 10:
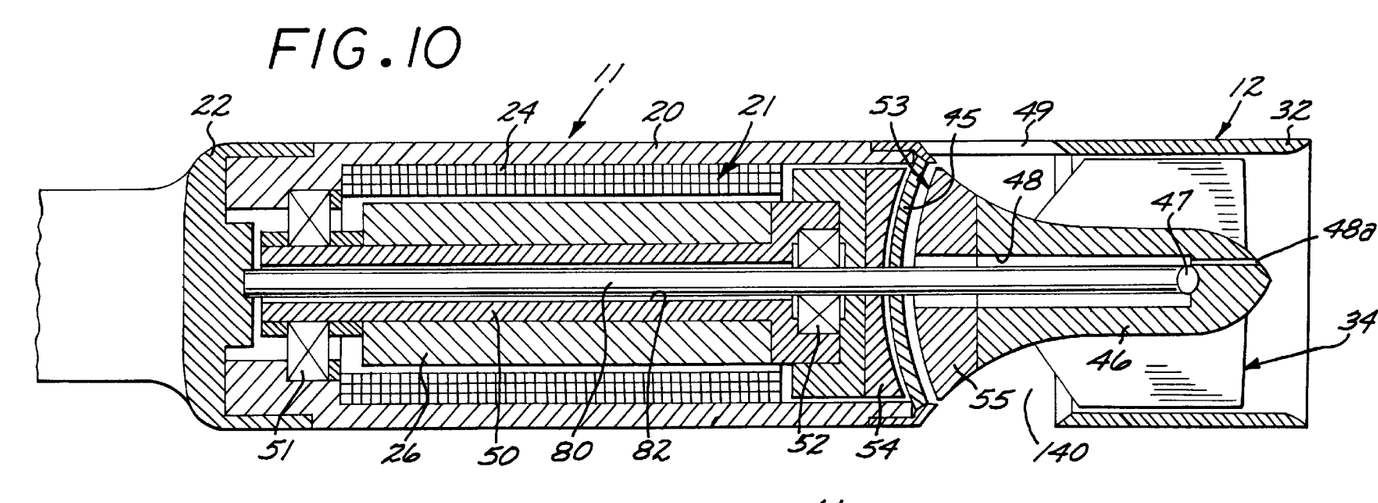
FIG. 10 is a longitudinal cross-section of another embodiment of the present invention.

FIG. 10 depicts an exemplary embodiment of the present invention wherein the drive unit 11 is completely sealed so as to substantially alleviate any risk of leakage either from the drive unit into the patient or from the patient into the drive unit. A non-rotating, stationary shaft 80 extends through the entire drive unit from the end wall 22 through a sealing end wall 45 to protrude from the distal end of the motor housing 20. The motor shaft 50 which carries the rotor 26 has a central bore 82 formed therein through which the stationary shaft 80 extends. The motor shaft 50 is supported on its proximal end by bearing 51 which in turn is embedded within the motor housing. The distal end of motor shaft 50 is supported by bearing 52 which is carried by non-rotating shaft 80. The rotor carries a magnet 54 on its distal end which is rigidly connected thereto and is positioned to spin adjacent to the non-magnetic end wall 45. The distal end of the shaft 80 protrudes into the pump housing 32 to support the hub 46 of impeller 34. Because the shaft does not rotate, a hermetic seal is readily formed at its interface with end wall 45. The hub is rotatably supported on the end of the shaft by a combined axial/radial bearing 47 in the form of a sphere. Both the distal end of the shaft 80 as well as bore 48 have a conical depression formed therein to accommodate the bearing 47. The shaft 80 is received in an oversized bore so as to provide sufficient radial clearance to allow the hub 46 to pivot slightly about the axial/radial bearing 47. Like the adjoining walls of the magnet sections 54 and 55, the end wall 45 is arched toward the interior of the motor housing, whereby the axial/radial bearing 47 forms the center of the arch. The arched configuration enables the impeller to pivot about bearing 47 and automatically assume a centered position. A flushing bore 48a, which extends through the hub from its distal end to the bore 48, serves to conduct a continuous flow of pumping fluid through the bore 48 to prevent the formation of thrombi. The presence of fluid in the bore additionally serves to dampen any pivoting motion the hub may undergo as it self centers and thereby serves to automatically stabilize the rotating impeller. This allows extremely high rotational speeds to be achieved without impeller-to-housing contact.

The hub 46, and hence impeller, is rotatably coupled to the magnetic rotor within housing 20. A magnet 55 is rigidly connected to the hub 46 and serves to transfer rotation from the rotor to the impeller. The magnetic holding force of the coupling 53 is also sufficiently strong to overcome the force which urges the impeller 34 in a distal direction during operation such that the impeller 34 is held by its hub 46 on the shaft 25 exclusively by the magnet holding force. The particular embodiment illustrated employs a statorless design wherein the impeller is extended proximally and engages the hub 46 at a relatively shallow angle. Elimination of the fixed stator additionally reduces the number of connection points to the motor housing, each of which is an area of very low flow velocity and hence a growth site for thrombi formation. Moreover, elimination of the fixed stator reduces the overall parts count and construction complexity and thus serves to reduce total cost.

Figure 11:
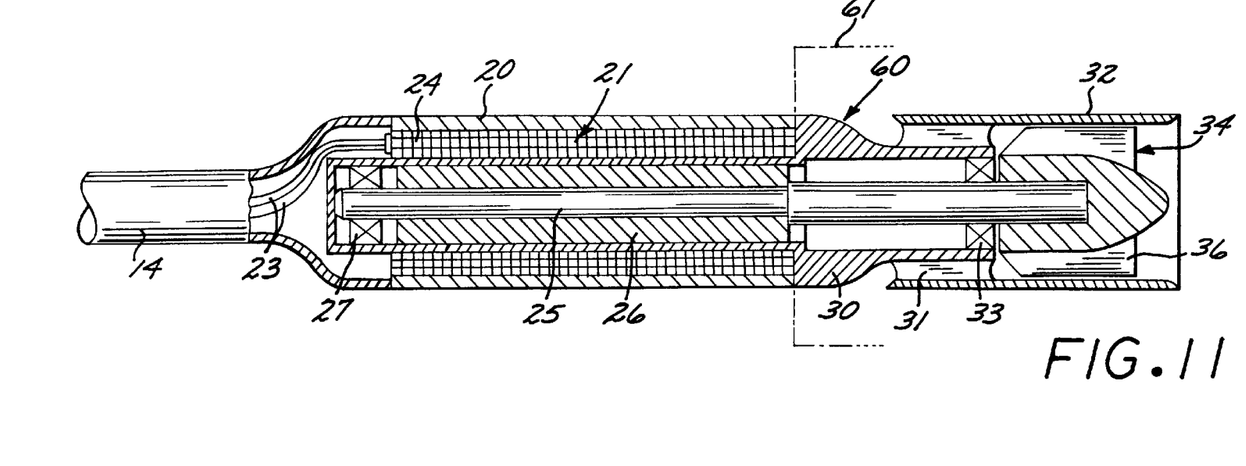
FIG. 11 is a longitudinal cross-section of yet another embodiment of the present invention.

The exemplary embodiment shown in FIG. 11 is similar to the embodiment illustrated in FIG. 4, however, the impeller 34, along with the shaft 25 and the rotor 26 as well as the tube 30 and the pump housing 32, forms a disposable unit, the boundaries of which are indicated by the broken line 61. The bearing 33 and bearing 27 also are part of the disposable unit. During use of the fluid pump, such pates become contaminated, and due to the various gaps, surface details, and recesses, complete decontamination is virtually impossible. The disposable unit 60 is made up of parts which may be manufactured relatively simply and inexpensively. They are removed as a unit from the motor housing 20 and disposed of after use to be replaced by another disposable unit. The remaining components, i.e. the housing, attached stator, and catheter are readily sterilized. As a result, the substantially more expensive components are reusable while the relatively inexpensive components are disposable.

Figure 12:
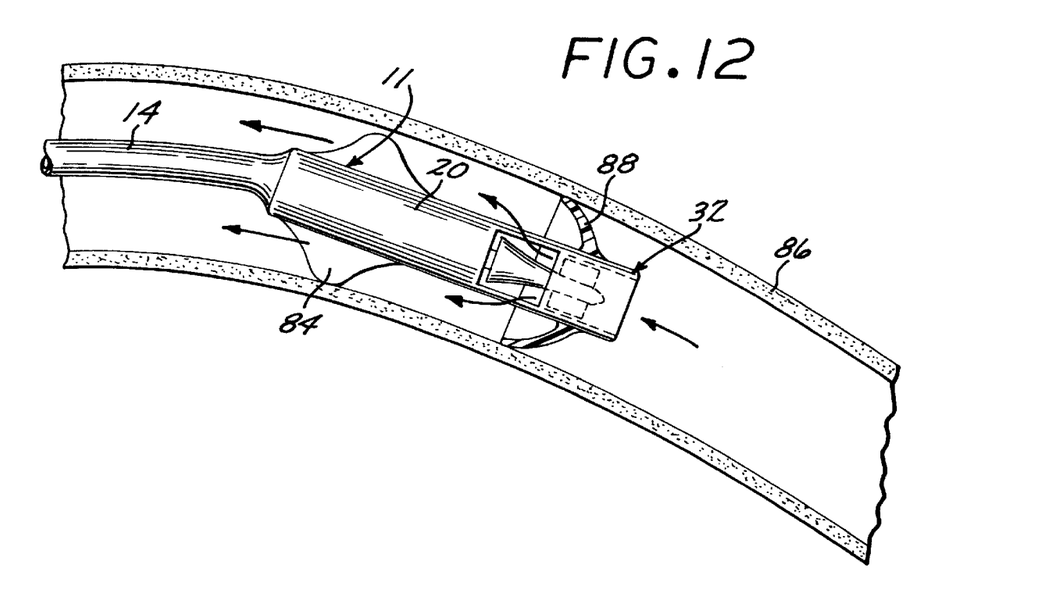
FIG. 12 is a schematic illustration of an alternate embodiment microaxial pump shown deployed within a vessel.
Figure 13:
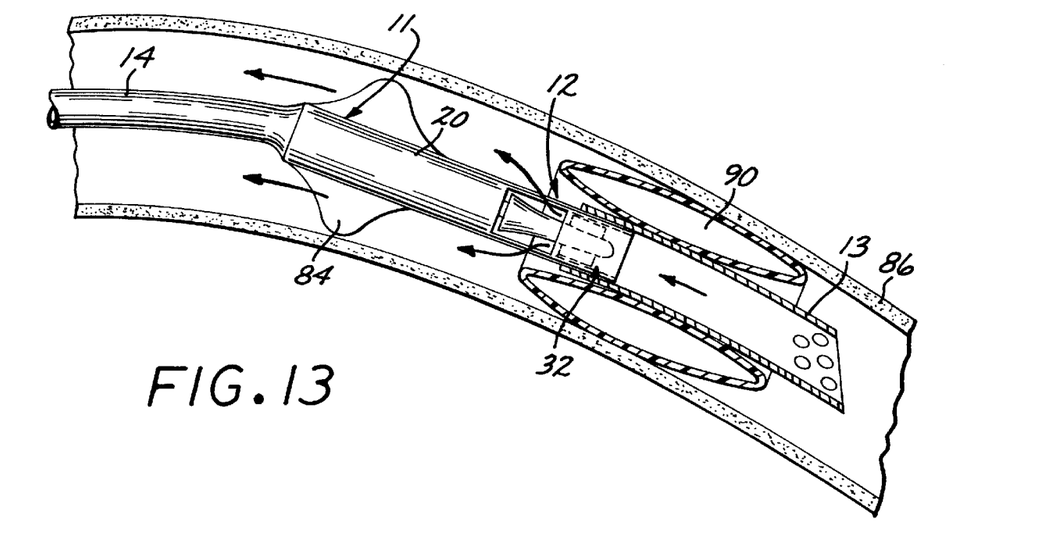
FIG. 13 is a schematic illustration of another alternative embodiment microaxial pump shown deployed within a vessel.

FIGS. 12 and 13 illustrate alternative embodiments of the fluid pump of the present invention that include components for centering the pump within the vasculature and stabilizing its position. Additionally, components are included that prevent backflow in order to boost the efficiency of the pump. Attached to the exterior of the drive unit housing 20 are at least three centering projections 84 that extend radially toward the vessel wall. Each projection consists of a spring-like rib which is optimally narrowed toward its outer end. The projections serve to center the device within the vessel to ensure that an adequate flowpath is maintained about its entire circumference.

In addition to the projections 84, FIG. 12 illustrates an embodiment that includes a flexible sealing element 88. The seal generally has the shape of a truncated cone and is attached to the pump housing 32 by its smaller distal end. Its larger, proximally extending end is expandable to engage the wall of the vessel 86 and conversely, is collapsible to lie against the pump housing 20. The seal 88 thus operates like a flap trap. When the pressure of fluid on the distal side is exceeded by the pressure on the proximal side, the sealing element expands to engage the surrounding vessel and seal the annular space between the pump housing and the vessel wall. This prevents backflow of the pumped fluid to boost efficiency. Should the fluid pressure on the distal side of the seal exceed the pressure on the proximal side, the seal collapses so as not to impede flow within the vessel. The seal's flexibility additionally allows the pump to be maneuvered within the vasculature without unnecessary resistance.

In the alternative embodiment shown in FIG. 13, an expandable annular balloon 90 is fitted about the pump housing 32. This balloon is in fluid communication with a lumen (not shown) of catheter 14 such that it can be inflated extracorporeally with gas or liquid. Upon inflation, the balloon expands to engage the surrounding vessel wall to prevent the backflow of fluid and additionally serves to center the pumping segment 12 and the attached inlet cannula 13 within the vessel. The centering projections 84 along with the inflatable balloon 90 additionally serve to effectively prevent rotation and axial migration of the entire pump device within the vessel.

Figure 14:
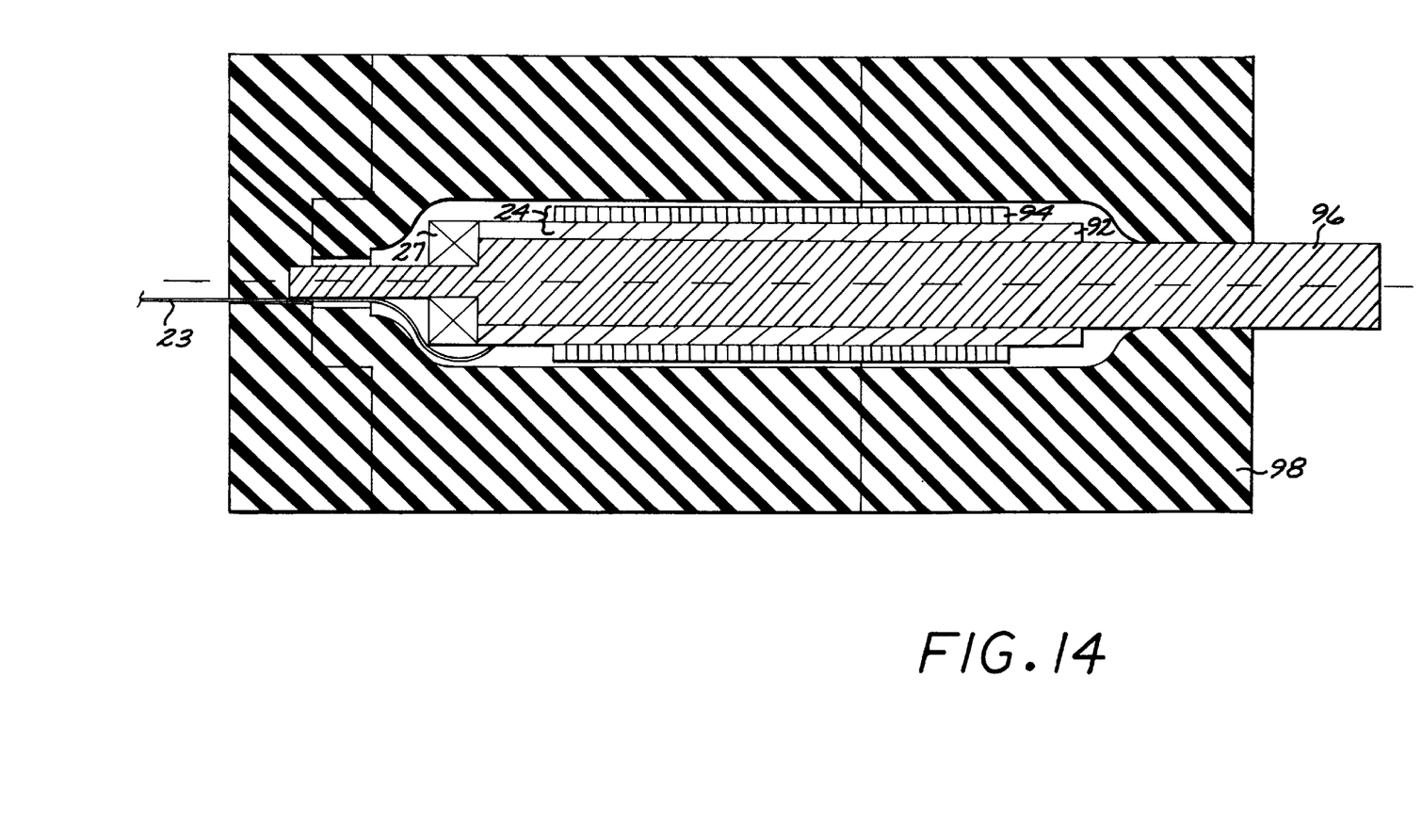
FIG. 14 is a cross-sectional view of drive unit components assembled within a mold.

FIG. 14 illustrates an efficient technique for manufacturing the drive unit and more specifically, the housing and stator components of such unit. Rather than laboriously assembling and aligning a multitude of extremely small, precision machined parts within the elongated housing shown in for example FIG. 4, the technique involves a relatively simple injection molding process. In the process, the interior windings 92 and outer lamination stack 94, which form the stator 24, along with conductors 23, are initially assembled about an assembly rod 96. The proximal bearing 27 is filled with wax to prevent the incursion of polymer, and is also affixed about the rod 96. The entire assembly is placed in and centered within an injection mold 98 afterwhich polymer is injected. The polymer permeates all of the void space to rigidly fix all of the aligned components in place and simultaneously form a casing equivalent to housing 20 such as for example in FIG. 4. After curing, the molding is removed from the mold and the assembly rod is removed from the molding. A housing/stator combination is thereby provided ready to receive the rotor and undergo final assembly. Less parts, including less machined pails, are needed, alignment is automatically achieved, the stator becomes integrated in the housing and the conductors are embedded and secured within the polymer. This method is substantially less labor intensive than heretofore employed methods and is readily adaptable to automation. The thin polymer motor housing does not impair heat transfer and is coated with polyurethane in order to achieve biocompatibility. Different dyes may be incorporated in the polymer in order to conveniently designate different pump sizes.

Figure 15:
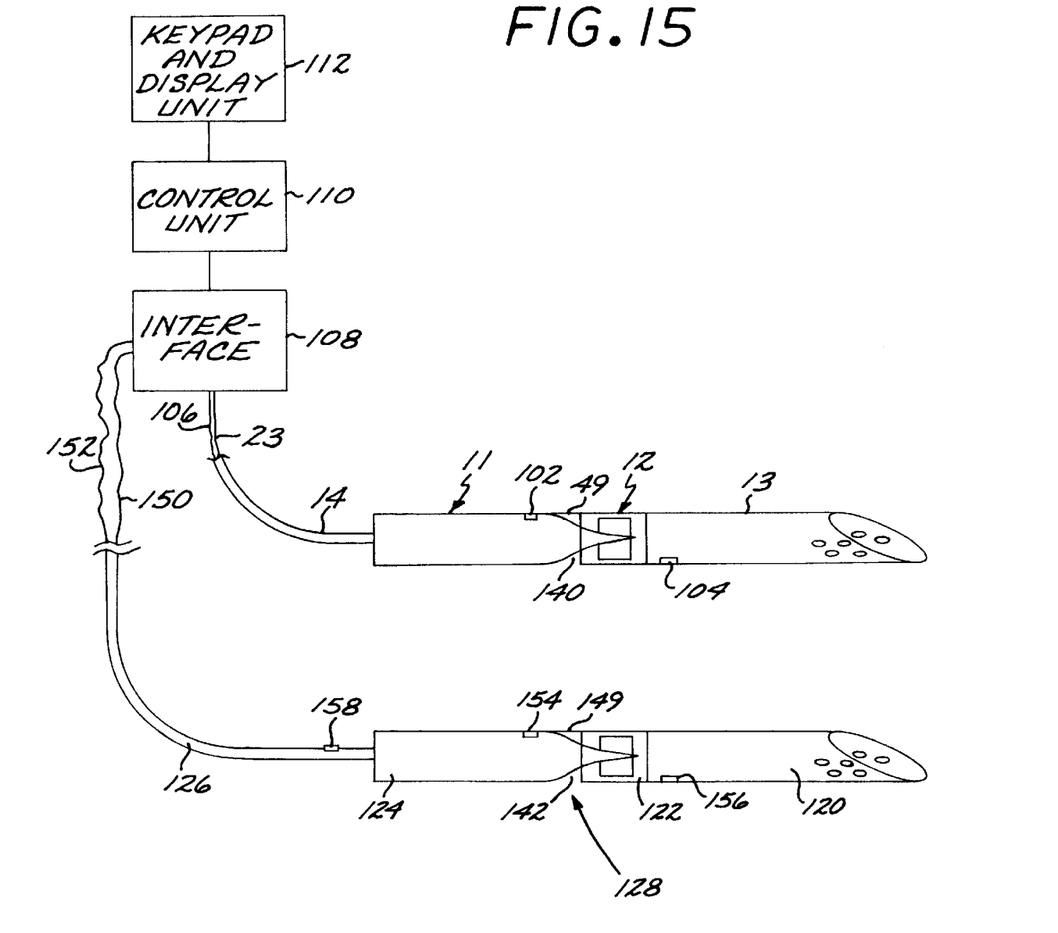
FIG. 15 is a schematic illustration of a system for controlling the operation of the microaxial pump.

FIG. 15 is a schematic representation of an alternative embodiment of the present invention wherein pressure sensors are fitted to the flow pump. More specifically, a first pressure sensor is attached to the surface of the drive unit 11 near the pumping segment discharge 140 while a second sensor 104 is fitted near the inlet to the pump housing. Sensor conductors 106 are incorporated in the pump components including for example, within, as for example in FIGS. 6 and 10, support 49 and extend through catheter 14 along with conductors 23, to set the sensors into communication with interface 108. A control module 110 receives and interprets the signals and controls the power conducted to the drive unit. Information relating to the current actually drawn by the motor is also provided to the control module. A keypad and display unit 112 is additionally interconnected with the control unit 110 to provide input and monitoring capability.

With the information provided by such sensors, it is possible to discern the position of the pump relative to the external sealing member such as the heart valve. Properly placed, a substantial pressure differential will be evident as the sensors will be sensing conditions on either side of the valve. Conversely, similar pressure readings are indicative of improper pump placement as both pressure sensors would be sensing conditions on the same side of the valve. Use of data generated by the two pressure sensors in addition to data relating to the current drawn by the motor provides additional information as to the placement and operation of the pump. By comparing the pressure differential to the current drawn by the motor, it is possible to identify blockage conditions as well as cavitation.

Alternatively, a second flow pump is fitted with sensors and interconnected to the control system to facilitate the coordinated operation of both pumps to optimize pumping performance. As illustrated in FIGS. 2 and 3, the first pump may for example be placed in the left ventricle while the second pump may be placed in the right ventricle. As shown in the FIG. 15, a first pressure sensor 154 is attached to the surface of the drive unit 124 near the pumping segment discharge 142 while a second sensor 156 is fitted near the inlet to the pump housing. Sensor conductors 150 are incorporated in the pump components including for example with support 149 and extend through catheter 126 along with the motor power conductor 150 to set the sensors into communication with the interface 108. Additional oxygen sensor 158 is fitted and interconnected with interface 108 to provide data reflecting the oxygenation of the blood.

Information relating to the inlet and outlet pressure along with the power consumption of the electric motor, provides a wealth of information relevant to the function of the pump device. In addition to providing a real time indication of flow rate, such data enables real time support for the task of pump placement potentially without the additional equipment needed for fluoroscopic techniques. Moreover, real time avoidance of conditions indicating the incipient onset of cavitation is possible while real time indications of flow blockage due to a blocked or collapsed inlet conduit or the formation of thrombi in the inlet, on the pump housing, or impeller signal the need for remedial action to be taken. The sensors also provide the capability of monitoring motor or pump wear or failure as well as the prediction of such events. Additionally, operation of the pump can be maintained with acceptable total hemolysis rates over the anticipated use period and output rate while pulsatile and non-pulsatile flow can be controlled. The performance trends of various parameters over many hours of operation can be displayed and analyzed while alarm features indicating conditions that need immediate attention facilitate operation with reduced supervision. Finally, the patient's heart can be monitored without removal of the pump.

Additionally, with the placement of two instrumented pumps it is possible for the control module to gain local information supplied by one pump to modify the operation of the second pump thereby facilitating optimization of the net output of the system as a whole.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An intravascular microaxial flow pump, comprising:
   a cylindrical drive unit of preselected outer diameter having an electric motor disposed therein driving a shaft distally extending therefrom wherein such shaft is supported by bearing located at the extreme proximal end of said drive unit and the extreme distal end of said drive unit;
   a cylindrical pump housing rigidly attached to said drive unit having essentially the same preselected outer diameter and oriented to be coaxially and distally disposed with respect to said drive unit;
   an impeller rotatably disposed within said pump housing, driven by said drive shaft, and operative to draw fluid into and through said housing and over drive unit;
   a first pressure sensor positioned on said drive unit so as to sense discharge pressure and generate a first signal indicative thereof;
   a second pressure sensor positioned on said pump housing so as to sense inlet pressure and generate a second signal indicative thereof; and
   a controller, configured for receiving said first signal generated by said first sensor and said second signal generated by said second sensor, processing said signals, and controlling the supply of power to said motor in accordance with such processed signals.

2. The pump of claim 1 further comprising a third sensor for sensing a load imposed on said electric motor wherein said controller is additionally configured to process said third signal and controlling the supply of power to said motor in accordance with such processed signals.

3. The pump of claim 1 further comprising a catheter proximally extending from said drive unit and housing electrical conductors extending from said controller to said electric motor.

4. The pump of claim 3, wherein said catheter additionally houses electrical conductors extending from said first sensor to said controller.

5. An intravascular microaxial flow pump, comprising:

a pump housing having an impeller rotatably disposed therein;

a first sensor operative to generate a first signal indicative of fluid conditions proximal to said impeller;

a second sensor operative to generate a second signal indicative of fluid conditions distal to said impeller;

a controller operative to receive and interpret said first and second signals and generate an output signal indicative of pumping performance.

6. The pump of claim 5, wherein said output signal is indicative of pump position.

7. The pump of claim 5, wherein said output signal is indicative of pump operation.

* * * * *

UNITED STATES PATENT AND TRADEMARK OFFICE
CERTIFICATE OF CORRECTION

PATENT NO. : 5,964,694
DATED : October 12, 1999
INVENTOR(S) : Thorsten Siess; and Helmut Reul It is certified that error appears in the above-identified patent and that said Letters Patent is hereby corrected as shown below:

Column 12, line 42, delete "bearing", and insert --bearings--;

Signed and Sealed this

Second Day of May, 2000

Attest:

Attesting Officer

Q. TODD DICKINSON
Director of Patents and Trademarks